(12) United States Patent
Bak et al.

(10) Patent No.: US 10,761,198 B2
(45) Date of Patent: Sep. 1, 2020

(54) METHOD AND APPARATUS FOR ACQUIRING IMAGE USING ULTRASOUND

(71) Applicant: SAMSUNG MEDISON CO., LTD., Hongcheon-gun (KR)

(72) Inventors: Ji-eun Bak, Hongcheon-gun (KR); Seung-ju Lee, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 790 days.

(21) Appl. No.: 15/366,156

(22) Filed: Dec. 1, 2016

(65) Prior Publication Data

US 2017/0153321 A1 Jun. 1, 2017

(30) Foreign Application Priority Data

Dec. 1, 2015 (KR) ........................ 10-2015-0170072

(51) Int. Cl.
| | |
|---|---|
| *A61B 8/00* | (2006.01) |
| *G01S 7/52* | (2006.01) |
| *G01S 15/89* | (2006.01) |
| *A61B 8/08* | (2006.01) |
| *G06T 7/00* | (2017.01) |

(52) U.S. Cl.
CPC ........ *G01S 7/52017* (2013.01); *A61B 8/4472* (2013.01); *A61B 8/463* (2013.01); *A61B 8/467* (2013.01); *A61B 8/485* (2013.01); *A61B 8/5276* (2013.01); *A61B 8/54* (2013.01); *A61B 8/565* (2013.01); *G01S 7/52042* (2013.01); *G01S 7/52071* (2013.01); *G01S 7/52073* (2013.01); *G01S 15/8915* (2013.01); *G01S 15/8977* (2013.01); *G06T 7/0016* (2013.01); *A61B 8/543* (2013.01); *G01S 7/52084* (2013.01); *G06T 2207/30096* (2013.01)

(58) Field of Classification Search
CPC .......... A61B 8/00; A61B 8/4472; A61B 8/463
See application file for complete search history.

(56) References Cited

U.S. PATENT DOCUMENTS

| 9,204,860 B2 | 12/2015 | Ji et al. | |
|---|---|---|---|
| 2008/0103392 A1* | 5/2008 | Seki .................. | A61B 8/08 600/437 |
| 2008/0188743 A1 | 8/2008 | Waki et al. | |
| 2010/0113930 A1 | 5/2010 | Miyachi | |
| 2012/0016237 A1 | 1/2012 | Tanigawa | |
| 2012/0253195 A1 | 10/2012 | Inoue et al. | |
| 2013/0083629 A1 | 4/2013 | Ji et al. | |
| 2013/0137983 A1 | 5/2013 | Shin et al. | |

(Continued)

FOREIGN PATENT DOCUMENTS

| JP | 4005856 B2 | 11/2007 |
|---|---|---|
| JP | 4588499 B2 | 12/2010 |
| WO | 2012086207 A1 | 6/2012 |

OTHER PUBLICATIONS

Communication dated May 15, 2017, issued by the European Patent Office in counterpart European Patent Application No. 16200300.8.

*Primary Examiner* — Joel F Brutus
(74) *Attorney, Agent, or Firm* — Sughrue Mion, PLLC

(57) ABSTRACT

Provided are an ultrasound apparatus and method of operating the same. The method comprises automatically obtaining an elasticity image by using a preset number of consistent and consecutive images and providing the obtained elasticity image.

18 Claims, 13 Drawing Sheets

(56) References Cited

U.S. PATENT DOCUMENTS

| | | |
|---|---|---|
| 2013/0150720 A1 | 6/2013 | Waki |
| 2013/0150721 A1 | 6/2013 | Kawabata et al. |
| 2014/0031685 A1 | 1/2014 | van der Steen et al. |
| 2015/0192547 A1* | 7/2015 | Lee .................. G01N 29/04 73/641 |
| 2015/0279025 A1* | 10/2015 | Waki .................. A61B 8/485 382/103 |

* cited by examiner

FIG. 14
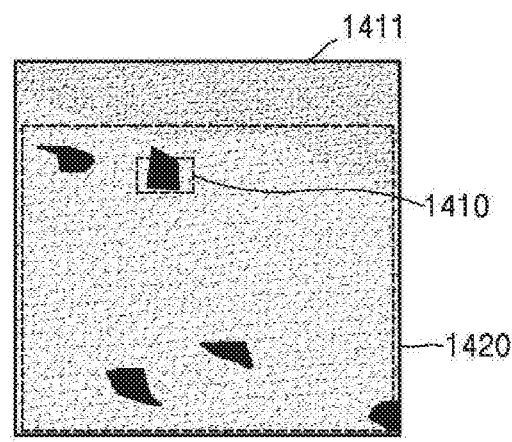
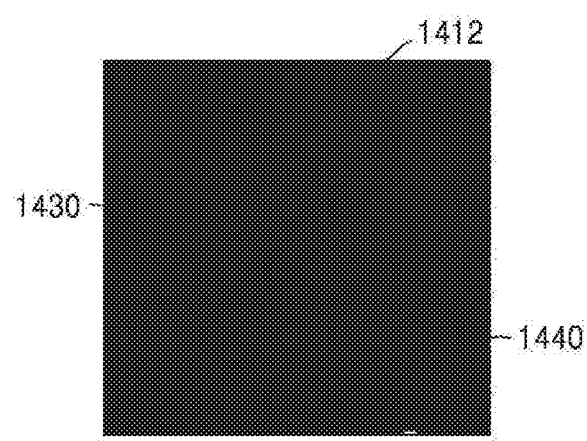

METHOD AND APPARATUS FOR ACQUIRING IMAGE USING ULTRASOUND

CROSS-REFERENCE TO RELATED APPLICATION

This application claims the benefit of Korean Patent Application No. 10-2015-0170072, filed on Dec. 1, 2015, in the Korean Intellectual Property Office, the disclosure of which is incorporated herein in its entirety by reference.

BACKGROUND

1. Field

The present disclosure relates to methods and apparatuses for acquiring an image by using ultrasound.

2. Description of the Related Art

Ultrasound imaging apparatuses transmit ultrasound signals generated by transducers of a probe to an object and receive echo signals reflected from the object, thereby obtaining at least one image of an internal part of the object (e.g., soft tissues or blood flow). In particular, ultrasound imaging apparatuses are used for medical purposes including observation of the interior of an object, detection of foreign substances, and diagnosis of damage to the object. Such ultrasound imaging apparatuses provide high stability, display images in real time, and are safe due to the lack of radioactive exposure, compared to X-ray apparatuses. Therefore, ultrasound imaging apparatuses are widely used together with other imaging apparatuses including a computed tomography (CT) apparatus, a magnetic resonance imaging (MRI) apparatus, and the like.

Such ultrasound imaging apparatuses calculate an elasticity value that is a measure of elasticity of an object and provide the elasticity value to a user. Elasticity of the object is related to pathological phenomena in the object.

SUMMARY

Provided are methods and ultrasound imaging apparatuses for providing a user with an elasticity image, and more particularly, methods of providing an elasticity image by using a plurality of images and ultrasound imaging apparatuses therefor.

Additional aspects will be set forth in part in the description which follows and, in part, will be apparent from the description, or may be learned by practice of the presented embodiments.

According to an aspect of an embodiment, a method of acquiring an image by using ultrasound waves includes: acquiring a preset number of consecutive images of an object by using the ultrasound waves; determining a variation representing a difference between the acquired consecutive images over time by performing a comparison between each of the consecutive images and its temporally adjacent image; and comparing the determined variation to a preset value and obtaining, based on a result of the comparing, an elasticity image of the object by using the consecutive images.

The method may further include displaying the obtained elasticity image.

The obtaining of the elasticity image of the object by using the consecutive images may include obtaining, if the variation is less than or equal to the preset value, the elasticity image of the object by using the consecutive images.

The method may further include, before the acquiring of the consecutive images, receiving a user input for setting an operating mode with respect to whether the elasticity image is to be automatically obtained. The obtaining of the elasticity image by using the consecutive images may include obtaining, if the variation is less than or equal to the preset value, the elasticity image of the object by using the consecutive images according to the operating mode set based on the user input.

The determining of the variation may include determining the variation by using changes in shape of the object between the consecutive images and/or changes in distribution of elasticity values therebetween.

The acquiring of the consecutive images may include acquiring the preset number of consecutive images of the object by using the ultrasound waves and storing the acquired consecutive images in a temporary memory.

The consecutive images may include a brightness (B) mode image.

The obtaining of the elasticity image of the object by using the consecutive images may include obtaining the elasticity image by using an elastography technique.

The determining of the variation may include determining the variation by performing the comparison between the consecutive images with a higher priority being placed on the overall change between the consecutive images than on individual changes between entities in the consecutive images.

The method may further include, after the obtaining of the elasticity image of the object by using the consecutive images, outputting, when the elasticity image is obtained, a signal indicating that the elasticity image is obtained, by using at least one of vision, hearing, and a tactile sense.

According to an aspect of another embodiment, an ultrasound apparatus for acquiring an image by using ultrasound waves includes: an image acquisition unit configured to acquire a preset number of consecutive images of an object by using the ultrasound waves; and a controller configured to determine a variation representing a difference between the acquired consecutive images over time by performing a comparison between each of the consecutive images and its temporally adjacent image and to compare the determined variation to a preset value and obtain, based on a result of the comparing, an elasticity image of the object by using the consecutive images.

The ultrasound apparatus may further include a transceiver configured to transmit ultrasound signals to the object and receive echo signals generated in response to the transmitted ultrasound signals from the object, and the image acquisition unit may acquire the consecutive images by using the echo signals.

The ultrasound apparatus may further include an output unit configured to display the obtained elasticity image.

The controller may obtain, if the variation is less than or equal to the preset value, the elasticity image of the object by using the consecutive images.

The ultrasound apparatus may further include a user interface unit configured to receive, before the acquiring of the consecutive images, a user input for setting an operating mode with respect to whether the elasticity image is to be automatically obtained, and the controller may obtain, if the variation is less than or equal to the preset value, the elasticity image of the object by using the consecutive images according to the operating mode set based on the user input.

The controller may determine the variation by using changes in shape of the object between the consecutive images and/or changes in distributions of elasticity values therebetween.

The controller may store the preset number of consecutive images of the object in a temporary memory by using the ultrasound waves.

The consecutive images may include a B mode image.

The controller may determine the variation by performing the comparison between the consecutive images with a higher priority being placed on the overall change between the consecutive images than on individual changes between entities in the consecutive images.

The ultrasound apparatus may further include an output unit configured to output, when the elasticity image is obtained, a signal indicating that the elasticity image is obtained, by using at least one of vision, hearing, and a tactile sense.

According to an aspect of another embodiment, a non-transitory computer-readable recording medium has recorded thereon a program for executing the method of acquiring an image by using ultrasound waves on a computer.

According to the embodiments, a method and apparatus for providing an elasticity image by using a plurality of ultrasound images may be provided.

BRIEF DESCRIPTION OF THE DRAWINGS

These and/or other aspects will become apparent and more readily appreciated from the following description of the embodiments, taken in conjunction with the accompanying drawings in which:

FIG. 14 is a diagram for explaining an example in which an ultrasound apparatus performs a comparison between acquired images, according to an embodiment.

DETAILED DESCRIPTION

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software. Expressions such as "at least one of," when preceding a list of elements, modify the entire list of elements and do not modify the individual elements of the list.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Hereinafter, embodiments will be described in detail with reference to attached drawings.

Figure 1:
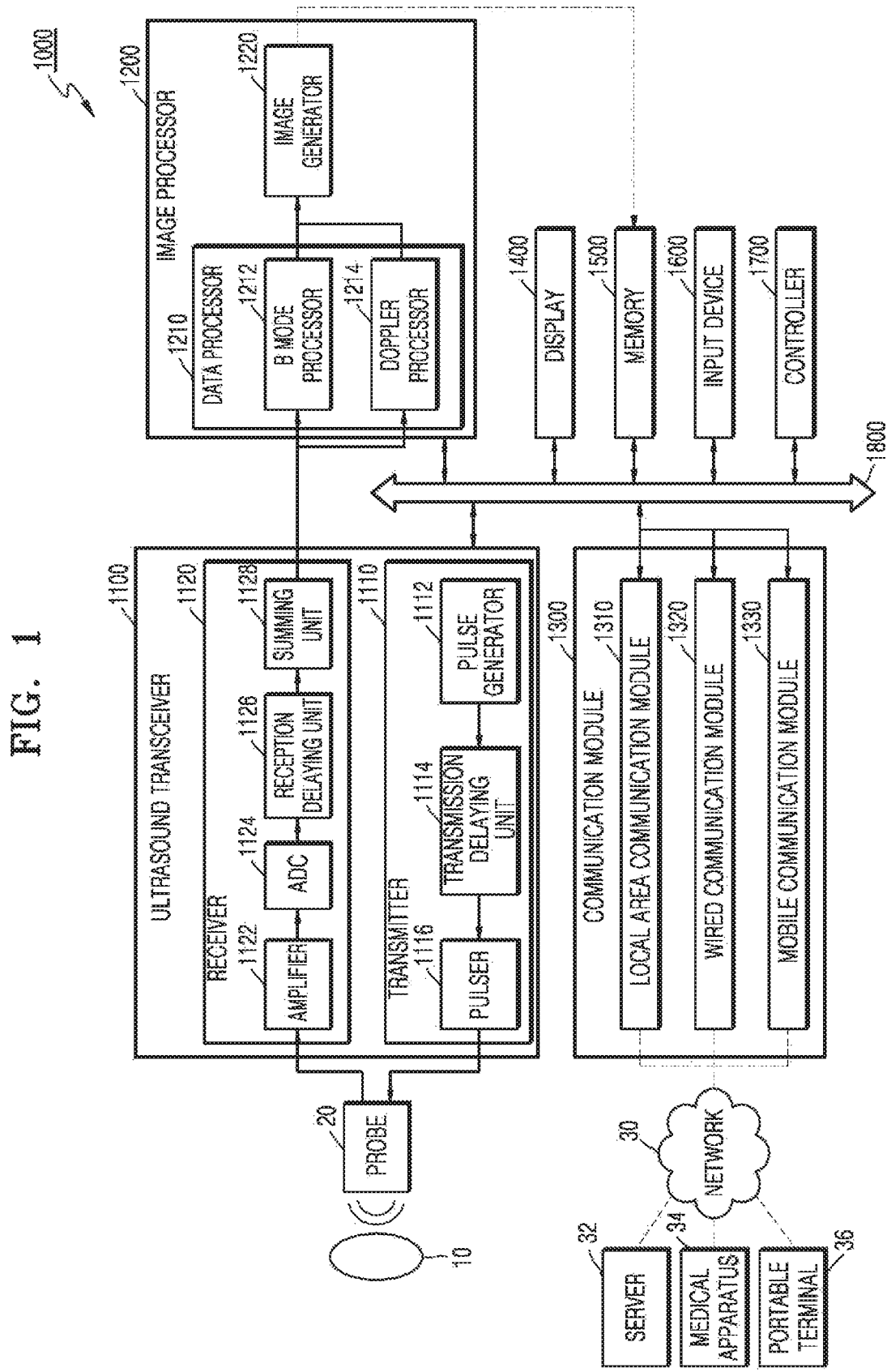
FIG. 1 is a block diagram of a configuration of an ultrasound diagnosis apparatus according to an embodiment.

FIG. 1 is a block diagram showing a configuration of an ultrasound diagnosis apparatus 1000 according to an embodiment. Referring to FIG. 1, the ultrasound diagnosis apparatus 1000 may include a probe 20, an ultrasound transceiver 1100, an image processor 1200, a communication module 1300, a display 1400, a memory 1500, an input device 1600, and a controller 1700, which may be connected to one another via buses 1800.

The ultrasound diagnosis apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly, and according to embodiments, the ultrasound diagnosis apparatus 1000 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined) pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 124 by delay times necessary for determining reception directionality, and the summing unit 1128 generates ultrasound data by summing the echo signals processed by the reception delaying unit 1166. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 included in a data processor 1210 extracts B mode components from ultrasound data and processes the B mode components. An image generator 1220 may generate an ultrasound image indicating signal intensities as brightness based on the extracted B mode components 1212.

Similarly, a Doppler processor 1214 included in the data processor 1210 may extract Doppler components from ultrasound data, and the image generator 1220 may generate a Doppler image indicating a movement of an object as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 1400 according to embodiments.

The communication module 1300 is connected to a network 30 by wire or wirelessly to communicate with an external device or a server. The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000. For example, the memory 1500 may store medical data related to diagnosis of an object, such as ultrasound data and an ultrasound image that are input or output, and may also store algorithms or programs which are to be executed in the ultrasound diagnosis apparatus 1000.

The memory 1500 may be any of various storage media, e.g., a flash memory, a hard disk drive, EEPROM, etc. Furthermore, the ultrasound diagnosis apparatus 1000 may utilize web storage or a cloud server that performs the storage function of the memory 1500 online.

The input device 1600 refers to a means via which a user inputs data for controlling the ultrasound diagnosis apparatus 1000. The input device 1600 may include hardware components, such as a keypad, a mouse, a touch pad, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound diagnosis apparatus 1000. In other words, the controller 1700 may control operations among the probe 20, the ultrasound transceiver 1100, the image processor 1200, the communication module 1300, the display 1400, the memory 1500, and the input device 1600 shown in FIG. 1.

All or some of the probe 20, the ultrasound transceiver 1100, the image processor 1200, the communication module 1300, the display 1400, the memory 1500, the input device 1600, and the controller 1700 may be implemented as software modules. Furthermore, at least one selected from the ultrasound transceiver 1100, the image processor 1200, and the communication module 1300 may be included in the controller 1600. However, embodiments of the present invention are not limited thereto.

Figure 2:
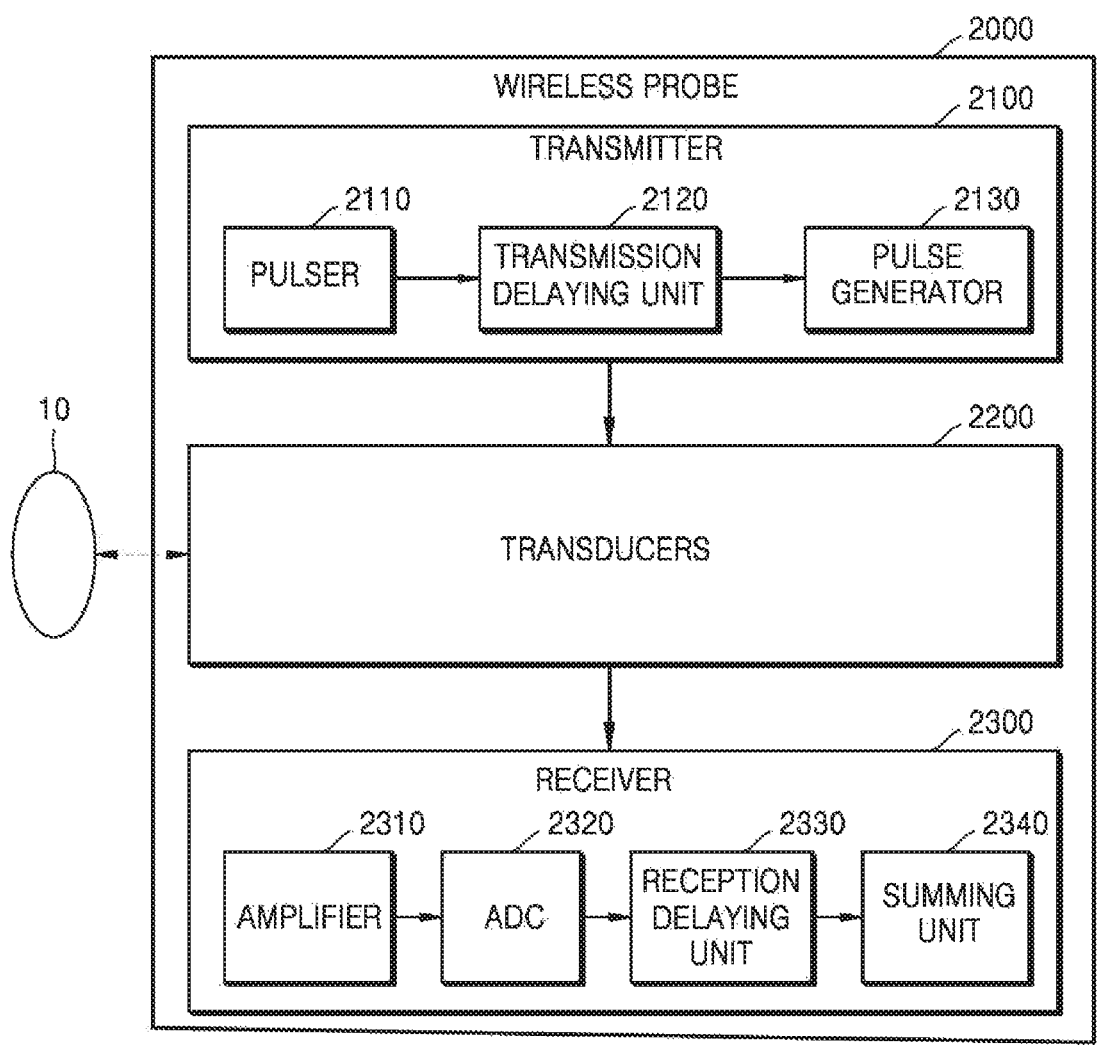
FIG. 2 is a block diagram of a configuration of a wireless probe according to an embodiment.

FIG. 2 is a block diagram showing a configuration of a wireless probe 2000 according to an embodiment. As described above with reference to FIG. 1, the wireless probe 2000 may include a plurality of transducers, and, according to embodiments, may include some or all of the components of the ultrasound transceiver 100 shown in FIG. 1.

The wireless probe 2000 according to the embodiment shown in FIG. 2 includes a transmitter 2100, a transducer 2200, and a receiver 2300. Since descriptions thereof are given above with reference to FIG. 1, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound diagnosis apparatus 1000 shown in FIG. 1.

An ultrasound apparatus for obtaining an elasticity image according to an embodiment will now be described in more detail with reference to FIGS. 3 through 14.

Figure 3:
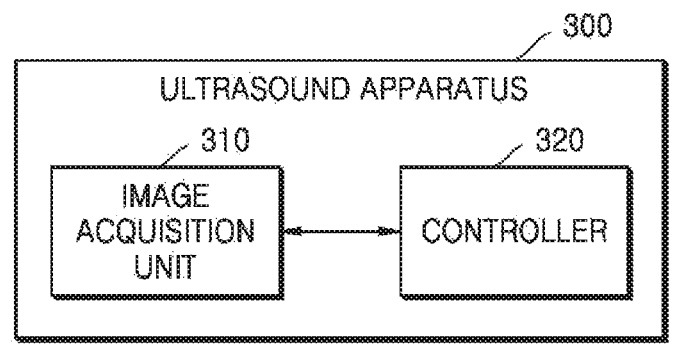
FIG. 3 is an example of a block diagram of a configuration of an ultrasound apparatus according to an embodiment.

FIG. 3 is an example of a block diagram of a configuration of an ultrasound apparatus 300 according to an embodiment.

Referring to FIG. 3, the ultrasound apparatus 300 according to the present embodiment may include an image acquisition unit 310 and a controller 320. However, the ultrasound apparatus 300 may include more or fewer components than those shown in FIG. 3.

The image acquisition unit 310 and the controller 320 may respectively correspond to the image processor 1200 and the controller 1700 shown in FIG. 1. In detail, the ultrasound apparatus 300 may be included in or correspond to the ultrasound imaging apparatus 1000.

The image acquisition unit 310 and the controller 320 will now be described in more detail.

According to an embodiment, the image acquisition unit 310 acquires a preset number of consecutive images of an object by using ultrasound waves. In the present specification, an image may include an ultrasound image.

For example, the image acquisition unit 310 may acquire a plurality of images of an object by performing continuous ultrasound imaging on the object by using ultrasound waves. For example, the image acquisition unit 310 may transmit ultrasound signals to a region of the object including a region of interest (ROI) and receive echo signals reflected from the region of the object, thereby obtaining an image of the object.

According to an embodiment, the image acquisition unit 310 may transmit ultrasound signals to an ROI and receive echo signals reflected from the ROI. The ROI may be a region in an ultrasound image obtained by using the echo signals. For example, the ROI may be of a square shaped area having a center at a predetermined position and a width and length both of 2 cm, but is not limited thereto. In detail, the ROI may be set to also have a rectangular, circular, or other polygonal shape.

According to an embodiment, the image acquisition unit 310 may transmit ultrasound signals to an ROI and receive echo signals reflected from the ROI. For example, the image acquisition unit 310 may transmit ultrasound signals at a frequency in the range between 2 MHz and 18 MHz to an ROI. The transmitted ultrasound signals may be partially reflected from layers between many different tissues. The image acquisition unit 310 may receive echo signals reflected in this way and obtain an image of the ROI by using electrical pulses generated based on the received echo signals.

According to an embodiment, the image acquisition unit 310 may continuously acquire images of an ROI by using echo signals reflected after ultrasound signals are transmitted to the ROI. For example, the image acquisition unit 310 may acquire twenty (20) images of the ROI per second, and embodiments are not limited thereto.

According to an embodiment, the image acquisition unit 310 may acquire a preset number of consecutive images of an object, which are then stored in a memory. For example, the image acquisition unit 310 may acquire a preset number of consecutive images of an object, which are then stored in a temporary memory. According to an embodiment, images stored in the temporary memory may be deleted after an elasticity image is obtained.

According to an embodiment, an image acquired by the image acquisition unit 310 may include a brightness (B) mode image. As another example, the image acquired by the image acquisition unit 310 may include at least one of an amplitude (A) mode image, a B mode image, a motion (M) mode image, and a Doppler image.

According to an embodiment, the controller 320 may determine a variation representing a difference between images over time by performing a comparison between each of images and its temporally adjacent image.

An example in which the image acquisition unit 310 acquires first through fifth images for one (1) second is described. According to an embodiment, the image acquisition unit 310 may continuously acquire first through fifth images for one second. The controller 320 may perform a comparison between each of the first through fifth images and its temporally adjacent image. For example, the controller 320 may determine a first variation by comparing the first and second images with each other and a second variation by comparing the second and third images with each other. The controller 320 may also obtain a third variation by comparing the third and fourth images with each other and a fourth variation by comparing the fourth and fifth images with each other. The first and second variations may respectively indicate the degree of similarity of the second image with respect to the first image and the degree of similarity of the third image with respect to the second image. The third and fourth variations may respectively indicate the degree of similarity of the fourth image with respect to the third image and the degree of similarity of the fifth image with respect to the fourth image.

According to an embodiment, the controller 320 may determine variations representing differences among images over time by using images selected from among an acquired plurality of images according to a preset method.

For example, the controller 320 may determine variations by comparing odd-numbered images with one another. An example in which the image acquisition unit 310 acquires first through sixth x images. for one (1) second is described. According to an embodiment, the image acquisition unit 310 may continuously acquire first through sixth x images for one second. The controller 320 may determine a first x variation by comparing the first and third x images with each other and a second x variation by comparing the third and fifth x images with each other. The first x variation may indicate the degree of similarity of the third x image with respect to the first x image. The second x variation may indicate the degree of similarity of the fifth x image with respect to the third x image.

As another example, the controller 320 may determine variations by comparing even-numbered images with one another. An example in which the image acquisition unit 310 acquires first through sixth y images for one (1) second is described. According to an embodiment, the image acquisition unit 310 may continuously acquire first through sixth y images for one second. The controller 320 may determine a first y variation by comparing the second and fourth images with each other and a second y variation by comparing the fourth and sixth y images with each other. The first y variation may indicate the degree of similarity of the fourth y image with respect to the second y image. The second y variation may indicate the degree of similarity of the sixth y image with respect to the fourth y image.

As another example, the controller 320 may determine variations by comparing images, which are selected via sampling, with one another. An example in which the image acquisition unit 310 acquires first through ninth z images for one (1) second is described. According to an embodiment, the image acquisition unit 310 may continuously acquire first through ninth z images for one second. The controller 320 may determine a first z variation by comparing the third and sixth z images with each other and a second z variation by comparing the sixth and ninth z images with each other. The first z variation may indicate the degree of similarity of the sixth z image with respect to the third z image. The second z variation may indicate the degree of similarity of the ninth z image with respect to the sixth z image.

As another example, the controller 320 may determine variations by comparing even-numbered images with each other and odd-numbered images with each other. An example in which the image acquisition unit 310 acquires first through fourth a images for one (1) second is described. According to an embodiment, the image acquisition unit 310 may continuously acquire first through fourth a images for one second. The controller 320 may determine a first a variation by comparing the first and third a images with each other and a second a variation by comparing the second and fourth a images with each other. The first a variation may indicate the degree of similarity of the third a image with respect to the first a image. The second a variation may indicate the degree of similarity of the fourth a image with respect to the second a image.

As another example, the controller 320 may classify an acquired plurality of images into a plurality of sets and determine a variation by comparing average values for images in each of the plurality of sets. Each of the plurality of sets may include consecutive or non-consecutive images. An example in which the image acquisition unit 310 acquires first through fourth b images for one (1) second is described. According to an embodiment, the image acquisition unit 310 may continuously acquire first through fourth b images for one second. According to an embodiment, the controller 320 may acquire a first b average image that is an average image of the first through third b images and a second b average image that is an average image of the second through fourth b images. The controller 320 may then compare the first b average image with the second b average image and determine a variation based on a result of the comparison. Alternatively, the controller 320 may acquire a first c average image that is an average image of the first and third b images and a second c average image that is an average image of the second and fourth b images. The controller 320 may then compare the first c average image with the second c average image and determine a variation based on a result of the comparison.

As another example, the controller 320 may determine a variation by using only certain images while excluding some of an acquired plurality of images. In this case, according to an embodiment, the controller 320 may perform a freeze operation by using only the non-excluded images. According to an embodiment, performing a freeze operation may include obtaining an elasticity image. According to an embodiment, the controller 320 may acquire a plurality of images, determine an average value of a predetermined property for the acquired plurality of images, exclude an image having a property value that is outside a preset range with respect to the obtained average value among the plurality of images, and obtain an elasticity value by using the non-excluded images. For example, the controller 320 may acquire a plurality of images, obtain an average brightness value of 10 for the acquired plurality of images, exclude an image having a brightness value greater than or equal to 12 or less than or equal to 8 among the plurality of images, and obtain an elasticity image by using non-excluded images. As another example, the controller 320 may acquire a plurality of images, obtain an average brightness value of 10 for the acquired plurality of images, exclude images having maximum and minimum brightness values among the plurality of images, and obtain an elasticity image by using non-excluded images. According to an embodiment, a property value may include a numerical value of a preset property of an image, such as brightness or color, and may be obtained from the entire image, a part of the image, or a pixel at a preset position in the image.

According to an embodiment, the controller 320 may determine a variation by using changes in shape of an object between images.

For example, the controller 320 may determine a first variation by comparing a first shape that is a shape of an object shown in a first image with a second shape that is a shape of the object shown in a second image. According to an embodiment, the controller 320 may determine a first variation representing the degree to which a second image differs from a first image by comparing positions and/or shapes of a plurality of entities represented by at least one of a point, a line, and a plane in the first and second images.

According to an embodiment, the controller 320 may determine a variation by using changes in distribution of elasticity values between images.

For example, the controller 320 may determine a first variation by comparing a first distribution that is a distribution of elasticity values displayed in a first image with a second distribution that is a distribution of elasticity values displayed in a second image. According to an embodiment, the controller 320 may determine a first variation representing the degree to which a second image differs from a first image by comparing distributions of elasticity values represented by a shape or color in the first and second images.

According to an embodiment, the controller 320 may determine a variation by performing a comparison between images with a higher priority being placed on the overall change between images acquired by the image acquisition unit 310 than on individual changes between entities in the acquired images.

According to an embodiment, the controller 320 may perform a comparison between images. For example, the controller 320 may perform a comparison between first and second images. The controller 320 may determine a variation by performing a comparison between images with a higher priority being placed on the overall change between the images than on individual changes between entities in the images.

An example in which the controller 320 performs a comparison between first and second images will now be described in more detail.

According to an embodiment, the controller 320 may determine a degree of the overall change between the first and second images. For example, the controller 320 may determine whether the overall shape of the second image moves as compared to that of the first image and the degree of movement if the overall shape of the second image moves. If a region being measured moves as a whole due to shaking of hands of a measurer or other factors, the overall change between the first and second images may occur to a large extent.

According to an embodiment, the controller 320 may determine the degree of change between entities in the first and second images. For example, the controller 320 may determine entities in the second image respectively corresponding to entities in the first image and then the degree of change between corresponding entities in the first and second images. When a change occurs between entities in the first and second images due to a change inside the object (e.g., heartbeat), the change between the entities in the first and second images may occur to a large extent.

Furthermore, according to an embodiment, the controller 320 may determine a variation by performing a comparison between images with a higher priority being placed on the overall change between first and second images than on individual changes between entities in the first and second images.

According to another embodiment, the controller 320 may determine a variation by performing a comparison between images with a higher priority being placed on individual changes between entities in images acquired by the image acquisition unit 310 than on the overall change between the acquired images.

According to an embodiment, the controller 320 may perform a comparison between images. For example, the controller 320 may perform a comparison between first and second images. The controller 320 may determine a variation by performing a comparison between images with a higher priority being placed on a change between entities in images than on the overall change between the images.

An example in which the controller 320 performs a comparison between first and second images will now be described in more detail.

According to an embodiment, the controller 320 may determine a degree of the overall change between the first and second images. For example, the controller 320 may determine whether the overall shape of the second image moves as compared to that of the first image and the degree of movement if the overall shape of the second image moves. If a region being measured moves as a whole due to shaking of hands of a measurer, etc., the overall change between the first and second images may occur to a large extent.

According to an embodiment, the controller 320 may determine the degree of change between entities in the first and second images. For example, the controller 320 may determine entities in the second image respectively corresponding to entities in the first image and then the degree of change between corresponding entities in the first and second images. When a change occurs between entities in the first and second images due to a change inside the object (e.g., heartbeat), the change between the entities in the first and second images may occur to a large extent.

Furthermore, according to an embodiment, the controller 320 may determine a variation by performing a comparison between images with a higher priority being placed on individual changes between entities in first and second images than on the overall change between the first and second images.

According to an embodiment, the controller 320 compares a variation to a preset value and obtains, based on a result of the comparison, an elasticity image of an object by using images acquired by the image acquisition unit 310. For example, the controller 320 may determine whether the variation is less than or equal to the preset value and obtain an elasticity image of the object by using images acquired by the image acquisition unit 310.

According to an embodiment, the controller 320 may determine whether a determined variation is less than or equal to a preset value.

For example, the controller 320 may determine whether a variation for a preset number of consecutive images acquired by the image acquisition unit 310 is less than or equal to a preset value. An example in which the number of consecutive images is preset to five (5) and the image acquisition unit 310 acquires first through fifth images for one (1) second is described. According to an embodiment, the controller 320 may determine first through fourth variations. The first and second variations respectively indicate the degree of similarity of the second image with respect to the first image and the degree of similarity of the third image with respect to the second image, and the third and fourth variations respectively indicate the degree of similarity of the fourth image with respect to the third image and the degree of similarity of the fifth image with respect to the fourth image. If the first through fourth variations are all less than or equal to a preset value, the controller 320 may determine that the determined variation is less than or equal to the preset value.

According to an embodiment, the controller 320 obtains an elasticity image of an object by using images acquired by the image acquisition unit 310, based on a result of the determining of whether the determined variation is less than or equal to the preset value. For example, if a predetermined number of consistent images of an object are acquired, the controller 320 may obtain one or more elasticity images of the object by using the predetermined number of consistent images. In this case, 'consistent' may mean that variations respectively determined for the predetermined number of images of the object are all less than or equal to the preset value. An example in which the number of images is preset to five (5) and the image acquisition unit 310 acquires first through fifth images for one (1) second is described. According to an embodiment, the controller 320 may determine first through fourth variations. The first and second variations respectively indicate the degree of similarity of the second image with respect to the first image and the degree of similarity of the third image with respect to the second image. The third and fourth variations respectively indicate the degrees of similarity of the fourth image with respect to the third image and of the fifth image with respect to the fourth image. If the first through fourth variations are all less than or equal to a preset value, the controller 320 may determine that the first through fifth images are consistent.

According to an embodiment, the controller 320 may obtain an elasticity image of an object by using a predetermined number of consistent, consecutive images of the object.

According to an embodiment, an elasticity image may be an image containing elasticity information of the object. For example, the elasticity image may be an image of the object on which elasticity information is indicated using color.

The number of consistent, consecutive images needed to obtain an elasticity image may be preset to a certain value. For example, the number of images needed to obtain an elasticity image may be preset to sixty (60) according to the performance of the controller 320, but is not limited thereto.

According to an embodiment, the controller 320 may obtain an elasticity image by using an elastography technique. For example, the controller 320 may obtain a relative elasticity image by using a strain ration.

Figure 4:
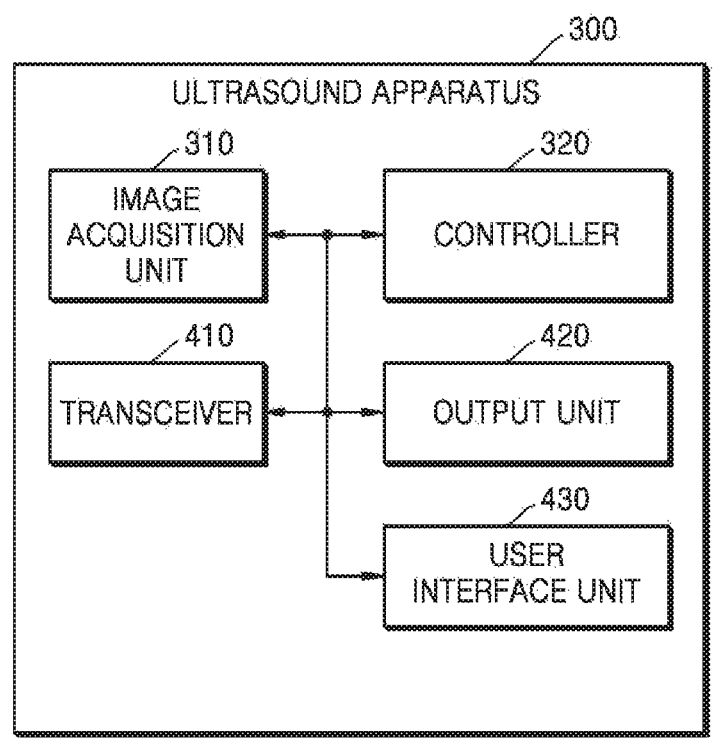
FIG. 4 is another example of a block diagram of a configuration of an ultrasound apparatus according to an embodiment.

FIG. 4 is another example of a block diagram of a configuration of an ultrasound apparatus 300 according to an embodiment.

Referring to FIG. 4, the ultrasound apparatus 300 according to the present embodiment may include an image acquisition unit 310, a controller 320, a transceiver 410, an output unit 420, and a user interface unit 430. However, the ultrasound apparatus 300 may include more or fewer components than those shown in FIG. 4.

In the ultrasound apparatus 300 of FIG. 4, the same components as those shown in FIG. 3 are denoted by the same reference numerals.

Unlike the ultrasound apparatus 300 of FIG. 3, the ultrasound apparatus 300 may further include the transceiver 410, the output unit 420, the user interface unit 430, and a communication module (not shown).

The transceiver 410, the output unit 420, the user interface unit 430, and the communication module will now be described in more detail.

The communication module may exchange data with at least one of an external server, an external medical apparatus, or an external portable terminal via a wired or wireless network. In detail, the communication module may correspond to the communication module 1300 shown in FIG. 1.

The ultrasound apparatus 300 may receive ultrasound data with respect to an object from an external medical apparatus such as a wireless probe (not shown) and obtain an ultrasound image or elasticity image based on the received ultrasound data. In this case, the communication module (not shown) may receive ultrasound data from the wireless probe via a wireless network.

According to an embodiment, the transceiver 410 may transmit ultrasound signals to the object and receive echo signals reflected from the object. For example, the transceiver 410 may transmit ultrasound signals to an ROI and receive echo signals reflected from the ROI.

According to an embodiment, the output unit 420 may include a display (not shown). The display included in the output unit 420 may correspond to the display 1400 shown in FIG. 1.

When an elasticity image is obtained, the output unit 420 may output a signal indicating that the elasticity image is obtained by using at least one of vision, hearing, and a tactile sense.

For example, when an elasticity image is obtained, the output unit 420 may display an indication that the elasticity image is obtained via a display screen included therein.

As another example, when an elasticity image is obtained, the output unit 420 may output a sound indicating that the elasticity image is obtained.

As another example, when an elasticity image is obtained, the output unit 420 may output a vibration indicating that the elasticity image is obtained via a probe connected thereto.

According to an embodiment, the user interface unit 430 may receive a user input, and the controller 320 may determine one operating mode from among a plurality of preset operating modes based on the received user input.

According to an embodiment, the user interface unit 430 may receive a user input based on a preset method. For example, the user interface unit 430 may receive a user input via a touch input. As another example, the user interface unit 430 may receive a user input via an input tool such as a mouse or keyboard. However, embodiments are not limited thereto, and the user interface unit 430 may also receive a user input by using methods other than those above.

Figure 5:
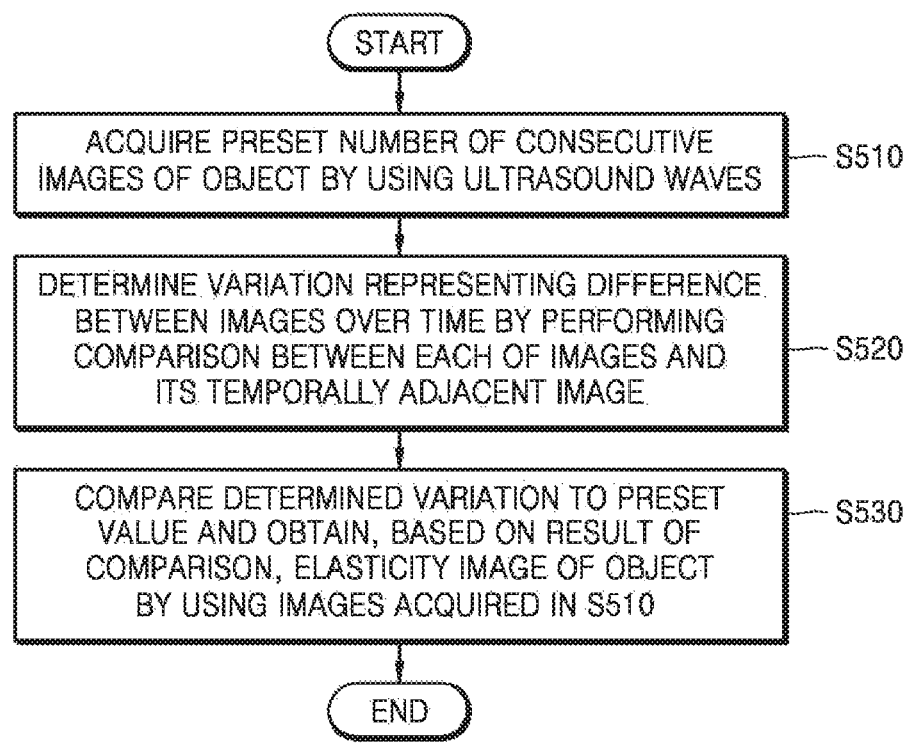
FIG. 5 is a flowchart of a method of obtaining an elasticity image, according to an embodiment.

FIG. 5 is a flowchart of a method of obtaining an elasticity image, according to an embodiment.

The ultrasound apparatus 300 acquires a preset number of consecutive images of an object by using ultrasound waves (S510). In the present specification, an image may include an ultrasound image.

For example, the ultrasound apparatus 300 may acquire a plurality of images of an object by performing continuous ultrasound imaging on the object by using ultrasound waves. For example, the ultrasound apparatus 300 may transmit ultrasound signals to a region of the object including an ROI and receive echo signals reflected from the region of the object, thereby obtaining an image of the object.

According to an embodiment, the ultrasound apparatus 300 may transmit ultrasound signals to an ROI and receive echo signals reflected from the ROI. The ROI may be a region in an ultrasound image obtained by using the echo signals. For example, the ROI may be of a square shape having a center at a predetermined position therein and with a width and a length of 2 cm, respectively, but is not limited thereto. In detail, the ROI may be set to have a square, circular, or other polygonal shape.

According to an embodiment, the ultrasound apparatus 300 may transmit ultrasound signals to an ROI and receive echo signals reflected from the ROI. For example, the ultrasound apparatus 300 may transmit ultrasound signals at a frequency in the range between 2 MHz and 18 MHz to an ROI. The transmitted ultrasound signals may be partially reflected from layers between many different tissues. The ultrasound apparatus 300 may receive echo signals reflected in this way and obtain an image of the ROI by using electrical pulses generated based on the received echo signals.

According to an embodiment, the ultrasound apparatus 300 may continuously acquire images of an ROI by using echo signals reflected after ultrasound signals are transmitted to the ROI. For example, the ultrasound apparatus 300 may acquire twenty (20) images of the ROI per second, and embodiments are not limited thereto.

According to an embodiment, the ultrasound apparatus 300 may acquire a preset number of consecutive images of an object and store the preset number of consecutive images of the object in a memory. For example, the ultrasound apparatus 300 may acquire a preset number of consecutive images of an object and store the preset number of consecutive images of the object in a temporary memory. According to an embodiment, images stored in the temporary memory may be deleted after an elasticity image is obtained.

According to an embodiment, the consecutive images acquired by the ultrasound apparatus 300 in operation S510 may include a B mode image. As another example, the consecutive images acquired by the ultrasound apparatus 300 in operation S510 may include at least one of an A mode image, a B mode image, an M mode image, and a Doppler image.

The ultrasound apparatus 300 determines a variation representing a difference between images over time by performing a comparison between each of images and its temporally adjacent image (S520).

An example in which the ultrasound apparatus 300 acquires first through fifth images for one (1) second is described. According to an embodiment, the ultrasound apparatus 300 may continuously acquire first through fifth images for one second. The ultrasound apparatus 300 may perform a comparison between each of the first through fifth images and its temporally adjacent image). For example, the ultrasound apparatus 300 may determine a first variation by comparing the first and second images with each other and a second variation by comparing the second and third images with each other. The ultrasound apparatus 300 may also determine a third variation by comparing the third and fourth images with each other and a fourth variation by comparing the fourth and fifth images with each other. The first and second variations may respectively indicate the degree of similarity of the second image with respect to the first image and the degree of similarity of the third image with respect to the second image. The third and fourth variations may respectively indicate the degree of similarity of the fourth image with respect to the third image and the degree of similarity of the fifth image with respect to the fourth image.

According to an embodiment, the ultrasound apparatus 300 may determine a variation by using a change in shape of an object between images.

For example, the ultrasound apparatus 300 may determine a first variation by comparing a first shape that is a shape of an object shown in a first image with a second shape that is a shape of the object shown in a second image. According to an embodiment, the ultrasound apparatus 300 may determine a first variation representing the degree to which a second image differs from a first image by comparing positions and/or shapes of a plurality of entities represented by at least one of a point, a line, and a plane in the first and second images.

According to an embodiment, the ultrasound apparatus 300 may determine a variation by using a change in distributions of elasticity values between images.

For example, the ultrasound apparatus 300 may determine a first variation by comparing a first distribution that is a distribution of elasticity values displayed in a first image with a second distribution that is a distribution of elasticity values displayed in a second image. According to an embodiment, the ultrasound apparatus 300 may obtain a first variation representing the degree to which a second image differs from a first image by comparing distributions of elasticity values represented by a shape or color in the first and second images.

According to an embodiment, the ultrasound apparatus 300 may determine a variation by performing a comparison between images with a higher priority being placed on the overall change between the images acquired in operation S510 than on individual changes between entities in the acquired images.

According to an embodiment, the ultrasound apparatus 300 may perform a comparison between images. For example, the ultrasound apparatus 300 may perform a comparison between first and second images. The ultrasound apparatus 300 may determine a variation by performing a comparison between images with a higher priority being placed on the overall change between the images than on individual changes between entities in the images.

An example in which the ultrasound apparatus 300 performs a comparison between first and second images will now be described in more detail.

According to an embodiment, the ultrasound apparatus 300 may determine the degree of the overall change between the first and second images. For example, the ultrasound apparatus 300 may determine whether the overall shape of the second image moves as compared to that of the first image and the degree of movement if the overall shape of the second image moves. If a region being measured moves as a whole due to shaking of hands of a measurer or other factors, the overall change between the first and second images may occur to a large extent.

According to an embodiment, the ultrasound apparatus 300 may determine the degree of change between entities in the first and second images. For example, the ultrasound apparatus 300 may determine entities in the second image respectively corresponding to entities in the first image and then the degree of change between corresponding entities in the first and second images. When a change occurs between entities in the first and second images due to a change inside the object (e.g., heartbeat), the change between the entities in the first and second images may occur to a large extent.

Furthermore, according to an embodiment, the ultrasound apparatus 300 may determine a variation by performing a comparison between images with a higher priority being placed on the overall change between first and second images than on individual changes between entities in the first and second images.

According to another embodiment, the ultrasound apparatus 300 may determine a variation by performing a comparison between images with a higher priority being placed on individual changes between entities in the images acquired in operation S510 than on the overall change between the acquired images.

According to an embodiment, the ultrasound apparatus 300 may perform a comparison between images. For example, the ultrasound apparatus 300 may perform a comparison between first and second images. The ultrasound apparatus 300 may determine a variation by performing a comparison between images with a higher priority being placed on individual changes between entities in images than on the overall change between the images.

An example in which the ultrasound apparatus 300 performs a comparison between first and second images will now be described in more detail.

According to an embodiment, the ultrasound apparatus 300 may determine a degree of the overall change between the first and second images. For example, the ultrasound apparatus 300 may determine whether the overall shape of the second image moves as compared to that of the first image and the degree of movement, if the overall shape of the second image moves. If a region being measured moves as a whole due to shaking of hands of a measurer, etc., the overall change between the first and second images may occur to a large extent.

According to an embodiment, the ultrasound apparatus 300 may determine the degree of change between entities in the first and second images. For example, the ultrasound apparatus 300 may determine entities in the second image respectively corresponding to entities in the first image and then the degree of change between corresponding entities in the first and second images. When a change occurs between entities in the first and second images due to a change inside the object (e.g., heartbeat), the change between the entities in the first and second images may occur to a large extent.

Furthermore, according to an embodiment, the ultrasound apparatus 300 may determine a variation by performing a comparison between images with a higher priority being placed on individual changes between entities in first and second images than on the overall change between the first and second images.

According to an embodiment, the ultrasound apparatus 300 compares the determined variation to a preset value and obtains, based on a result of the comparison, an elasticity image of the object by using the images acquired in operation S510 (S530). For example, the ultrasound apparatus 300 may determine whether the variation is less than or equal to the preset value and obtain an elasticity image of the object by using the images acquired in operation S510.

According to an embodiment, the ultrasound apparatus 300 may determine whether the variation determined in operation S520 is less than or equal to the preset value.

For example, the ultrasound apparatus 300 may determine whether a variation for the preset number of consecutive images acquired in operation S510 is less than or equal to the preset value. An example in which the number of consecutive images is preset to five (5) and the ultrasound apparatus 300 acquires first through fifth images for one (1) second is described. As described above with reference to operation S520, the ultrasound apparatus 300 may determine first through fourth variations. The first and second variations respectively indicate the degrees of similarity of the second image with respect to the first image and of the third image with respect to the second image, and the third and fourth variations respectively indicate the degrees of similarity of the fourth image with respect to the third image and of the fifth image with respect to the fourth image. If the first through fourth variations are all less than or equal to a preset value, the ultrasound apparatus 300 may determine that the variation obtained in operation S520 is less than or equal to the preset value.

According to an embodiment, the ultrasound apparatus 300 obtains an elasticity image of an object by using the images acquired in operation S510, based on a result of the determining of whether the variation determined in operation S520 is less than or equal to the preset value. For example, if a predetermined number of consistent images of an object are acquired, the ultrasound apparatus 300 may obtain one or more elasticity images of the object by using the predetermined number of consistent images. In this case, 'consistent' may mean that variations respectively determined for the predetermined number of images of the object are all less than or equal to the preset value. An example in which the number of images is preset to five (5) and the ultrasound apparatus 300 acquires first through fifth images for one (1) second is described. As described above with reference to operation S520, the ultrasound apparatus 300 may determine first through fourth variations. The first and second variations respectively indicate the degrees of similarity of the second image with respect to the first image and of the third image with respect to the second image. The third and fourth variations respectively indicate the degrees of similarity of the fourth image with respect to the third image and of the fifth image with respect to the fourth image. If the first through fourth variations are all less than or equal to a preset value, the ultrasound apparatus 300 may determine that the first through fifth images are consistent. However, examples in which a predetermined number of images of the object are considered as being 'consistent' are not limited thereto.

According to an embodiment, the ultrasound apparatus 300 may obtain an elasticity image of an object by using a predetermined number of consistent, consecutive images of the object.

According to an embodiment, an elasticity image may be an image containing elasticity information of the object. For example, the elasticity image may be an image of the object on which elasticity information is indicated in color.

The number of consistent, consecutive images needed to obtain an elasticity image may be preset to a certain value. For example, the number of images needed to obtain an elasticity image may be preset to sixty (60) according to the performance of the ultrasound apparatus 300, but is not limited thereto.

According to an embodiment, the ultrasound apparatus 300 may obtain an elasticity image by using an elastography technique. For example, in operation S530, the ultrasound apparatus 300 may obtain a relative elasticity image by using a strain ration.

When an elasticity image is obtained, the ultrasound apparatus 300 may output a signal indicating that the elasticity image is obtained by using at least one of vision, hearing, and a tactile sense.

For example, when an elasticity image is obtained, the ultrasound apparatus 300 may display an indication that the elasticity image is obtained, via a display screen included therein.

As another example, when an elasticity image is obtained, the ultrasound apparatus 300 may output a sound indicating that the elasticity image is obtained.

As another example, when an elasticity image is obtained, the ultrasound apparatus 300 may output a vibration indicating that the elasticity image is obtained via a probe connected thereto.

Figure 6:
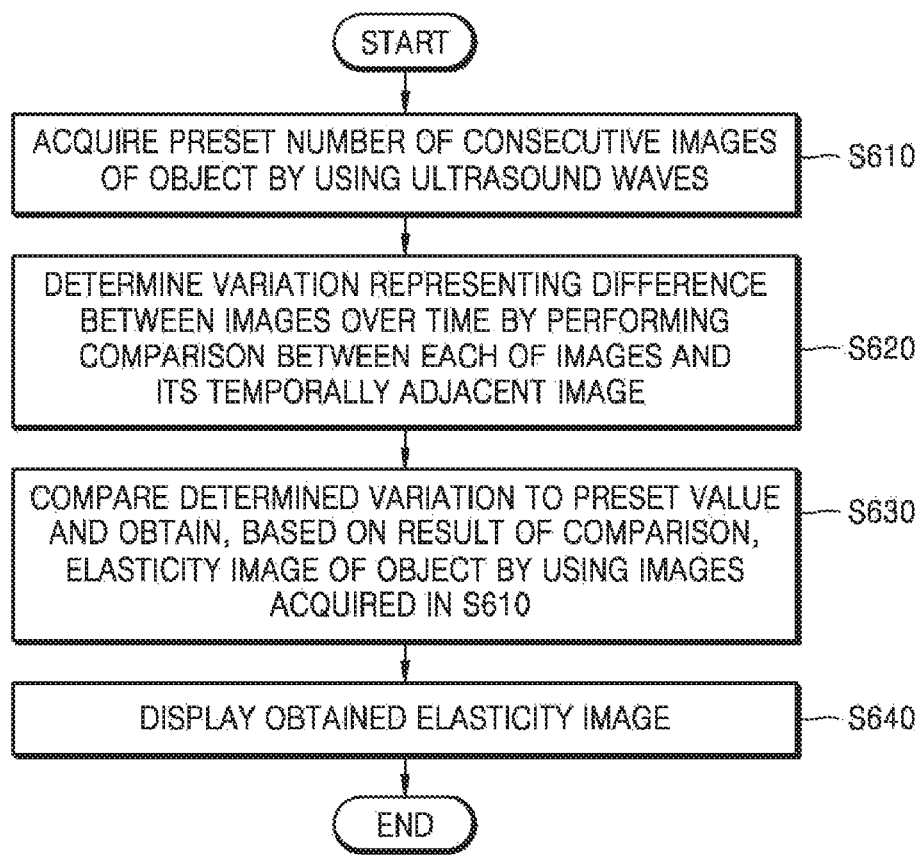
FIG. 6 is a flowchart of a method of obtaining an elasticity image and displaying the elasticity image, according to an embodiment.

FIG. 6 is a flowchart of a method of obtaining an elasticity image and displaying the elasticity image, according to an embodiment.

Since operations S610, S620, and S630 respectively correspond to operation S510, S520, and S530 described with reference to FIG. 5, descriptions that are already provided above with reference to FIG. 5 will be omitted here to simplify the overall descriptions.

The ultrasound apparatus 300 displays an elasticity image obtained in operation S630 (S640). According to an embodiment, the ultrasound apparatus 300 may include a display (not shown) for displaying an elasticity image. The display may be included in the output unit 420 described with reference to FIG. 4.

According to an embodiment, the ultrasound apparatus 300 may include a display (not shown), and the display may display the elasticity image obtained in operation S630. In this case, elasticity information may be indicated in color on the displayed elasticity image.

Figure 7:
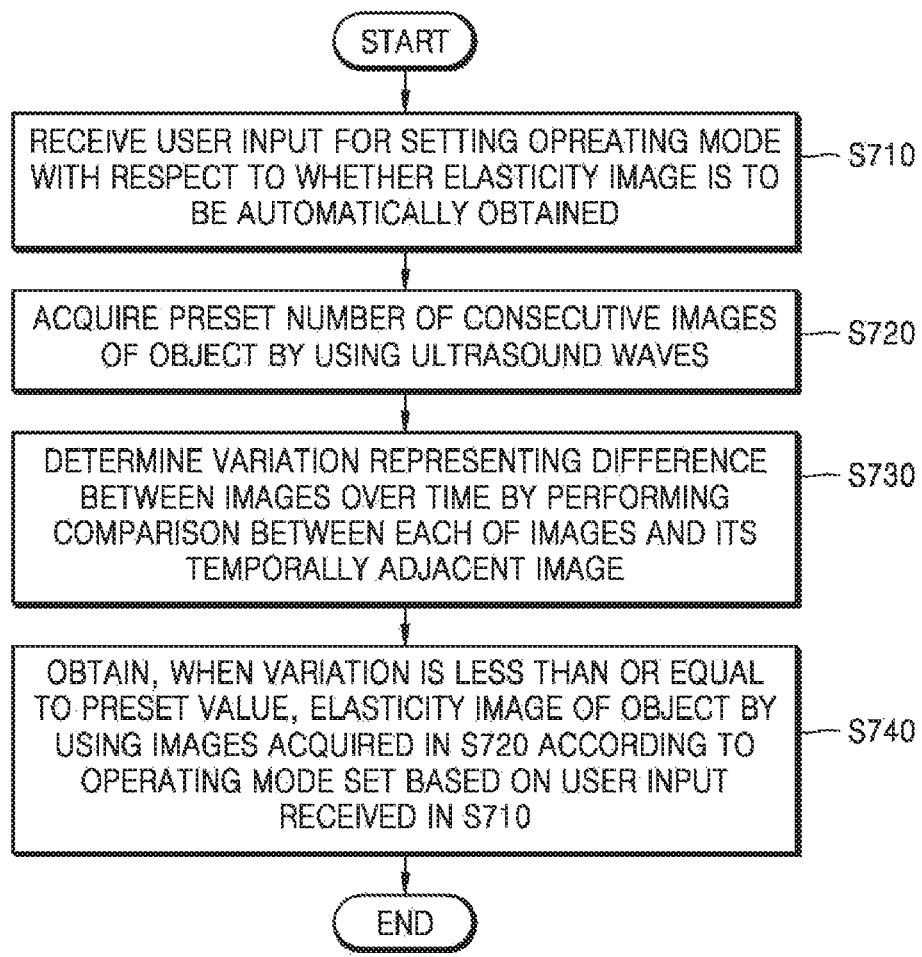
FIG. 7 is a flowchart of a method of obtaining an elasticity image after receiving a user input, according to an embodiment.

FIG. 7 is a flowchart of a method of obtaining an elasticity image after receiving a user input, according to an embodiment.

The ultrasound apparatus 300 receives a user input for setting an operating mode with respect to whether an elasticity image is to be automatically obtained (S710).

According to an embodiment, the ultrasound apparatus 300 may receive a user input and determine one operating mode from among a plurality of preset operating modes based on the received user input. For example, the ultrasound apparatus 300 may determine, based on a user input, one of an auto freeze mode and a manual freeze mode for an elasticity image.

The ultrasound apparatus 300 may receive a user input. The user input may be received based on a preset method. For example, the ultrasound apparatus 300 may receive a user input via a touch input. As another example, the ultrasound apparatus 300 may receive a user input via an input tool such as a mouse or keyboard. However, embodiments are not limited thereto, and the ultrasound apparatus 300 may receive a user input by using methods other than above.

Furthermore, as described above, the ultrasound apparatus 300 may receive a user input via the user interface unit 430.

The ultrasound apparatus 300 acquires a preset number of consecutive images of an object by using ultrasound waves (S720).

The ultrasound apparatus 300 determines a variation representing a difference between images over time by performing a comparison between each of images and its temporally adjacent image(S730).

Since operations S720 and S730 respectively correspond to operations S510 and S520 described with reference to FIG. 5, descriptions that are already provided above with reference to FIG. 5 will be omitted below to simplify the overall descriptions.

According to the operating mode set based on the user input received in operation S710, the ultrasound apparatus 300 obtains, when the variation is less than or equal to a preset value (S740), an elasticity image of the object by using the consecutive images acquired in operation S720.

For example, when an operating mode determined based on the user input received in operation S710 is an auto freeze mode and when it is determined in operation S730 that the variation is less than or equal to the preset value, the ultrasound apparatus 300 may obtain an elasticity image of the object by using the consecutive images acquired in operation S720 even when there is no additional user input.

As another example, when the operating mode determined based on the user input received in operation S710 is a manual freeze mode and even when it is determined in operation S730 that the variation is less than or equal to the preset value, the ultrasound apparatus 300 may not obtain an elasticity image of the object by using the consecutive images acquired in operation S720 unless there is an additional user input. For example, if the operating mode determined based on the user input received in operation S710 is a manual freeze mode and if it is determined in operation S730 that the variation is less than or equal to the preset value, the ultrasound apparatus 300 may display a message notifying that an elasticity image is to be obtained. After displaying the message, the ultrasound apparatus 300 may obtain, when a user input for obtaining an elasticity image is received, the elasticity image by using the consecutive images acquired in operation S720.

Figure 8:
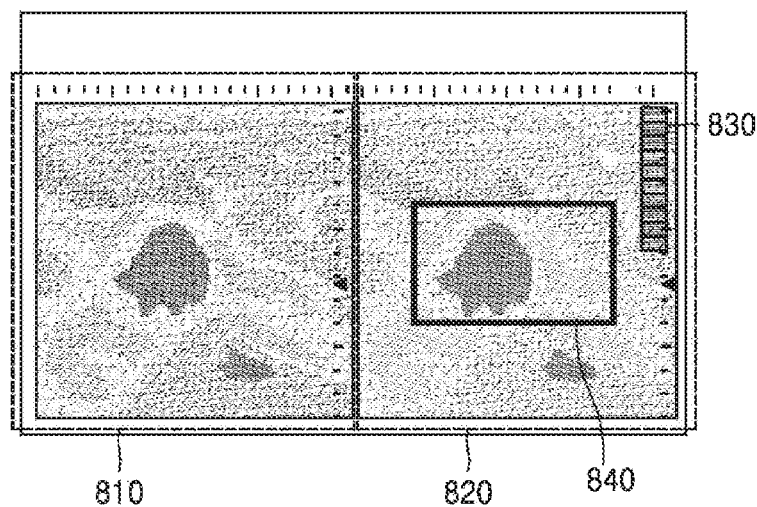
FIG. 8 is a diagram for explaining a method, performed by an ultrasound apparatus, of obtaining an ultrasound image, according to an embodiment.

FIG. 8 is a diagram for explaining a method, performed by the ultrasound apparatus 300, of obtaining an ultrasound image, according to an embodiment.

The ultrasound apparatus 300 may obtain an image of an object.

An image 810 on the left is an example of a screen generally displayed when an image of the object is obtained.

An image 820 on the right is an example of a screen displayed when the ultrasound apparatus 300 obtains an image of the object.

As seen on the image 820, the ultrasound apparatus 300 may display an ROI 840 on the screen.

According to an embodiment, the ultrasound apparatus 300 may transmit ultrasound signals to the ROI 840 and receive echo signals reflected from the ROI 840. The ROI 840 may be a region in an ultrasound image obtained by using the echo signals. For example, the ROI 840 may be set to have a rectangular shape having a center at a predetermined position and a width of 5 cm and a length of 2 cm, but is not limited thereto. In detail, the ROI may be set to have a square, circular, or other polygonal shape.

Furthermore, the ultrasound apparatus 300 may display a motion bar 830. According to an embodiment, the motion bar 830 may show the number of images currently acquired. For example, the motion bar 830 may indicate the number of consecutive images currently acquired and a degree of continuity among the currently acquired images.

According to an embodiment, a height of a bar that fills up the motion bar 830 in the longitudinal direction may represent the number of currently acquired, consecutive images, and a color of the bar filling up the motion bar 830 may represent the degree of continuity among the currently acquired images. For example, the bar that fills up the motion bar 830 may be divided into 10 smaller quadrangles, which means that ten (10) images have been obtained. As another example, the bar filling the motion bar 830 may be divided into smaller quadrangles, and a color of the quadrangles may represent a degree of consistency among ten images respectively corresponding to the quadrangles. In this case, red, yellow, and grass green colors may respectively indicate low consistency, medium consistency, and high consistency. As another example, the bar filling the motion bar 830 may be displayed as a filling gauge, and a height of the bar may be proportional to the number of acquired images. In this case, the filling gauge is not divided into quadrangles or other shapes.

Furthermore, the ultrasound apparatus 300 may operate as displayed in the motion bar 830. For example, if a bar fills up the motion bar 830 to six (6) quadrangles while preserving a grass green color, the ultrasound apparatus 300 may automatically perform a freeze operation even without receiving a user input. The freeze operation may include an operation of obtaining an elasticity image of the object.

Embodiments are not limited to the above-described examples of the motion bar 830.

Figure 9:
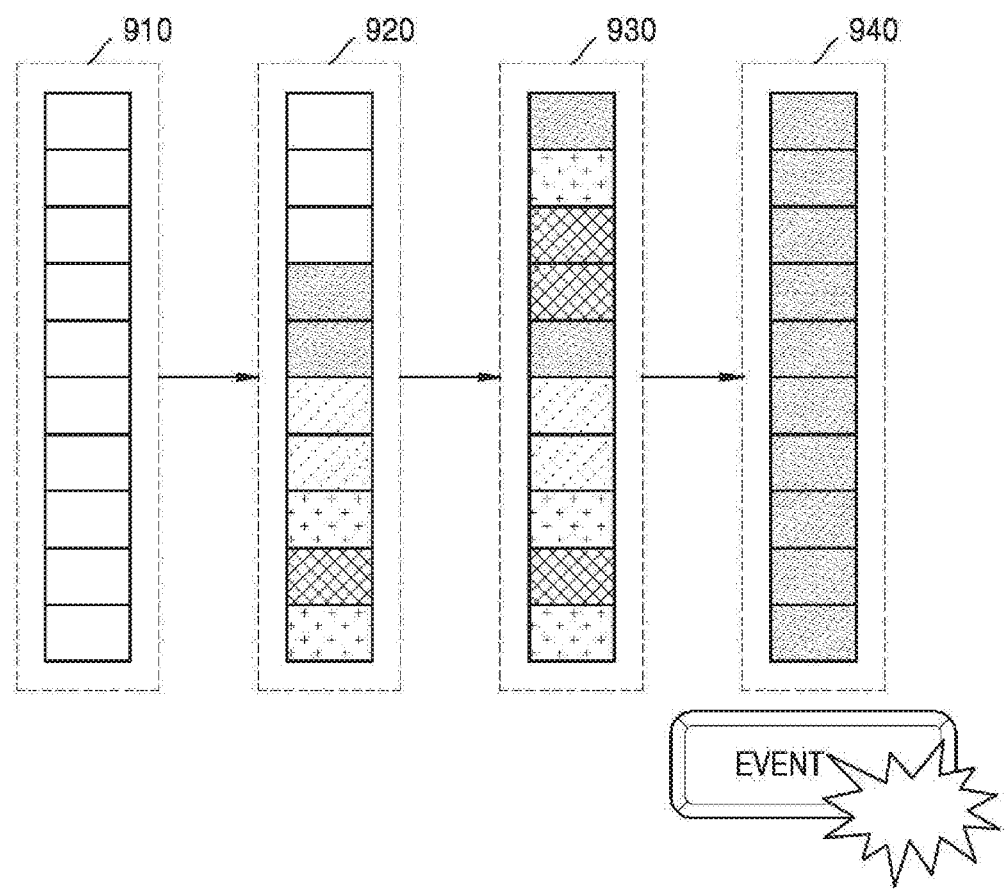
FIG. 9 is diagram for explaining an example in which an ultrasound apparatus obtains an elasticity image, according to an embodiment.

FIG. 9 is diagram for explaining an example in which the ultrasound apparatus 300 obtains an elasticity image, according to an embodiment.

Motion bars will now be described in more detail with reference to FIG. 9.

A first motion bar 910 may be a motion bar displayed when no image is acquired. In this case, since an entire outline of the first motion bar 910 is displayed but no quadrangles fill the first motion bar 910, the inside of the first motion bar 910 may be displayed as white.

A second motion bar 920 is a motion bar displayed when fewer than a preset number of images are acquired. When fewer than a preset number of images are acquired, the second motion bar 920 may display a bar that is filled up halfway. In this case, the number of currently acquired images against the preset number of images may be represented by a height of the bar filling the second motion bar 920. Furthermore, the second motion bar 920 may show a degree of consistency among the acquired images. For example, the second motion bar 920 may show the degree of consistency among the acquired images in different colors. For example, red, orange, yellow, and grass green colors may respectively indicate no consistency, low consistency, medium consistency, and high consistency.

A third motion bar 930 is a motion bar displayed when the same number of images as a preset number are acquired. When images whose number is greater than or equal to the preset number are acquired, the third motion bar 930 may display a bar that is completely filled. In this case, since the bar is filled up to a maximum height, this may indicate that a number of images greater than or equal to the preset number are acquired. Furthermore, the third motion bar 930 may show a degree of consistency among the acquired images. For example, the third motion bar 930 may show the degree of consistency among the acquired images in different colors. The third motion bar 930 may display the bar filled with quadrangles of different colors. In this case, since the preset number of images have been acquired, but consistency among the acquired images are not maintained, the ultrasound apparatus 300 does not perform a freeze operation.

A fourth motion bar 940 is also a motion bar displayed when the same number of images as a preset number are acquired. When a number of images greater than or equal to the preset number are acquired, the fourth motion bar 940 may display a bar that is completely filled. In this case, since the bar is filled up to a maximum height, this may indicate that a number of images greater than or equal to the preset number are acquired. Furthermore, the fourth motion bar 940 may show a degree of consistency among the acquired images. For example, the fourth motion bar 940 may show the degree of consistency among the acquired images in a particular color. The fourth motion bar 940 may display the bar filled with quadrangles of the same particular color. When the fourth motion bar 940 is completely filled with the same particular color indicating consistency, the ultrasound apparatus 300 may determine that the preset number of consistent, consecutive images are acquired. After determining that the preset number of consistent, consecutive images are acquired, the ultrasound apparatus 300 may perform a freeze operation without receiving an additional user input according to an operating mode set before acquisition of the images. For example, if an operating mode is set to an auto freeze mode and the ultrasound apparatus 300 determines that the preset number of consistent, consecutive images are acquired, the ultrasound apparatus 300 may perform a freeze operation without receiving an additional user input.

Figure 10:
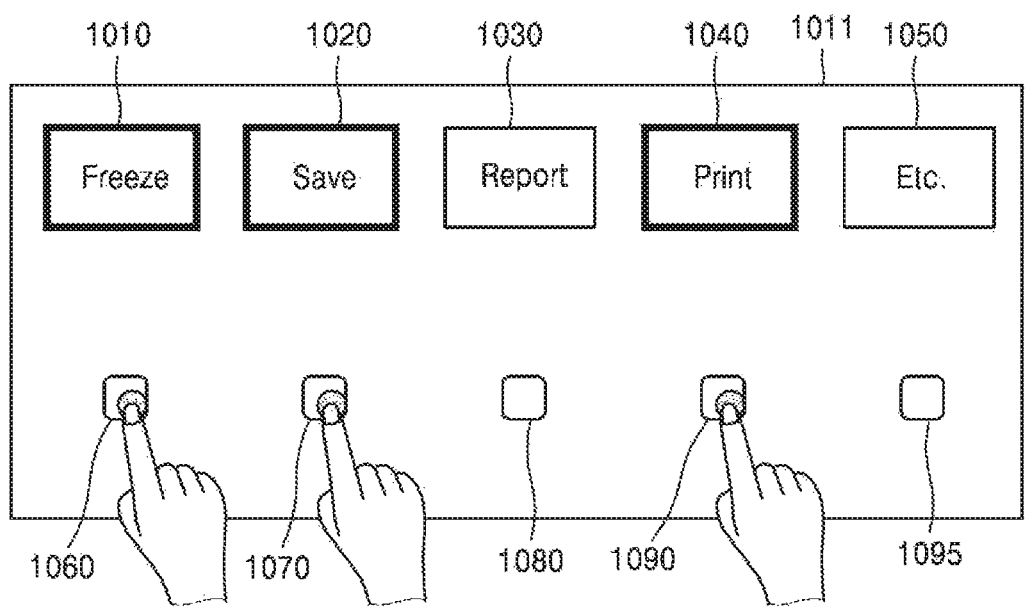
FIG. 10 is a diagram for explaining an example in which an ultrasound apparatus obtains a user input, according to an embodiment.

FIG. 10 is a diagram for explaining an example in which the ultrasound apparatus 300 obtains a user input, according to an embodiment.

The ultrasound apparatus 300 may display a screen 1011 as shown in FIG. 10.

According to an embodiment, the ultrasound apparatus 300 may display a plurality of menus 1010, 1020, 1030, 1040, and 1050. Furthermore, the ultrasound apparatus 300 may display a plurality of buttons 1060, 1070, 1080, 1090, and 1095 for respectively selecting the plurality of menus 1010, 1020, 1030, 1040, and 1050.

According to an embodiment, the ultrasound apparatus 300 may receive an input for selecting the plurality menus 1010, 1020, 1030, 1040, and 1050 from a user. For example, the ultrasound apparatus 300 may receive a touch input via at least one of the plurality of buttons 1060, 1070, 1080, 1090, and 1095 and set an operating mode corresponding to at least one of the plurality of menus 1010, 1020, 1030, 1040, and 1050.

For example, if the user performs a touch input on the first button 1060, the ultrasound apparatus 300 may receive the user touch input and determine a setting mode as being a mode in which an auto freeze operation is performed. For example, if the setting mode is determined as being a mode in which an auto freeze operation is performed, the ultrasound apparatus 300 may display an indication of selection of a setting mode corresponding to a first menu 1010. For example, the ultrasound apparatus 300 may display an edge in a preset color around the first menu 1010. According to an embodiment, when the setting mode is determined as being a mode for performing an auto freeze operation and when a preset number of consistent, consecutive ultrasound images are acquired, the ultrasound apparatus 300 may automatically perform a freeze operation to thereby obtain an elasticity image.

As another example, if the user performs a touch input on a second button 1070, the ultrasound apparatus 300 may receive the user touch input and determine a setting mode as being a mode in which a save operation is performed. For example, if the setting mode is determined as being a mode in which a save operation is performed, the ultrasound apparatus 300 may display an indication of selection of a setting mode corresponding to a second menu 1020. For example, the ultrasound apparatus 300 may display an edge in a preset color around the second menu 1020. According to an embodiment, when the setting mode is determined as being a mode for performing a save operation, the ultrasound apparatus 300 may store, when an elasticity image is obtained, the obtained elasticity image at a preset position.

As another example, if the user does not perform a touch input on a third button 1080, the ultrasound apparatus 300 may determine a setting mode as being a mode in which a report operation is not performed. For example, if the setting mode is not determined as being a mode for performing a report operation, the ultrasound apparatus 300 may display an indication that a setting mode corresponding to a third menu 1030 is not selected. For example, the ultrasound apparatus 300 may not display an edge in a preset color around the third menu 1030. According to an embodiment, when the setting mode is determined as being a mode in which a report operation is not performed and when an elasticity image is obtained, the ultrasound apparatus 300 may not display information related to the elasticity image.

As another example, if the user performs a touch input on a fourth button 1090, the ultrasound apparatus 300 may receive the user touch input and determine a setting mode as being a mode in which a print operation is performed. For example, if the setting mode is determined as being a mode for performing a print operation, the ultrasound apparatus 300 may display an indication of selection of a setting mode corresponding to a fourth menu 1040. For example, the ultrasound apparatus 300 may display an edge in a preset color around the fourth menu 1040. According to an embodiment, when the setting mode is determined as being a mode in which a print operation is performed and when an elasticity image is obtained, the ultrasound apparatus 300 may print the obtained elasticity image.

As another example, if the user does not perform a touch input on a fifth button 1095, the ultrasound apparatus 300 may determine a setting mode as being a mode in which an operation corresponding to the fifth button 1095 is not performed. For example, if the setting mode is not determined as being a mode in which the operation corresponding to the fifth button 1095 is performed, the ultrasound apparatus 300 may display an indication that a setting mode corresponding to a fifth menu 1050 is not selected. For example, the ultrasound apparatus 300 may not display an edge in a preset color around the fifth menu 1050. According to an embodiment, when the setting mode is determined as being a mode for not performing the operation corresponding to the fifth button 1095, the ultrasound apparatus 300 may not perform the operation corresponding to the fifth button 1095.

Figure 11:
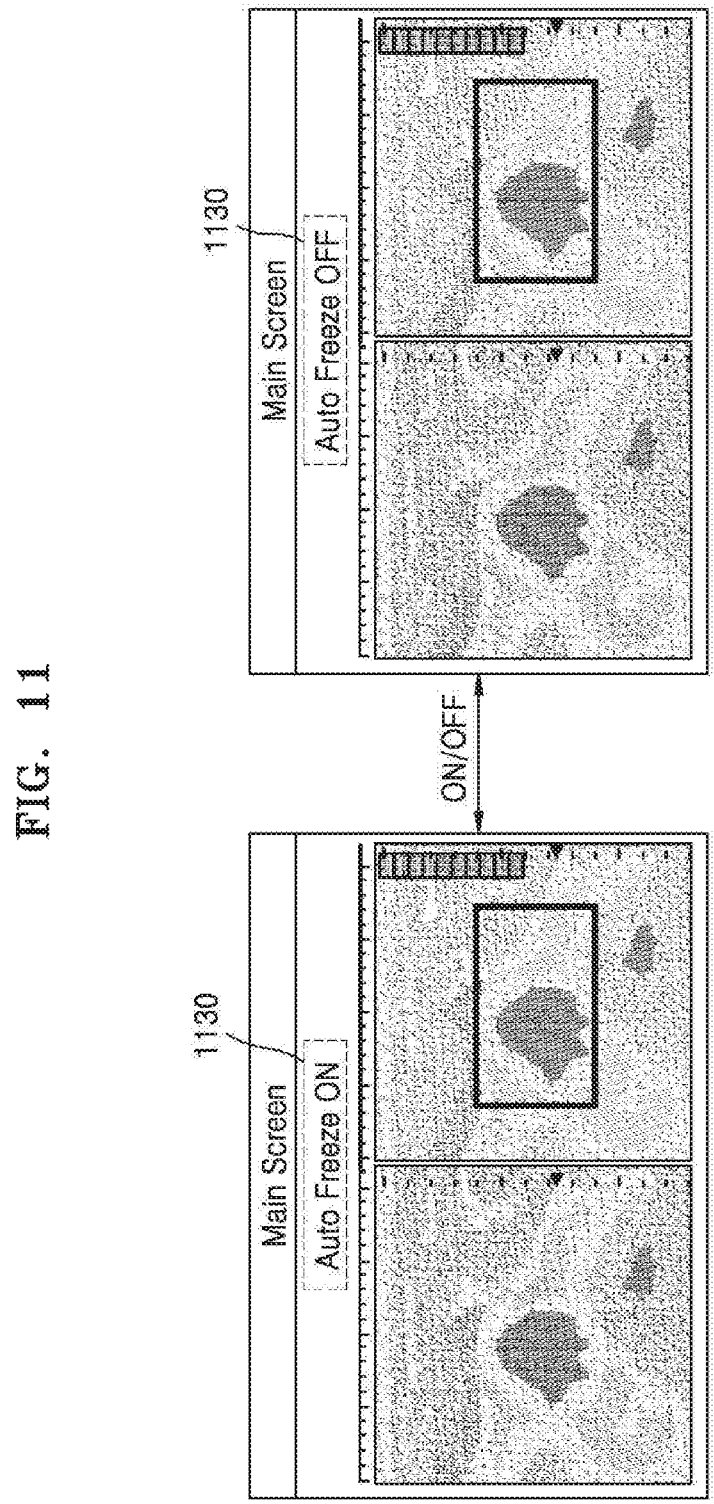
FIG. 11 is a diagram for explaining an example in which an ultrasound apparatus receives a user input and obtains an elasticity image, according to an embodiment.

FIG. 11 is a diagram for explaining an example in which the ultrasound apparatus 300 receives a user input and obtains an elasticity image, according to an embodiment.

For example, if a setting mode is determined as being a mode in which an auto freeze operation is performed, the ultrasound apparatus 300 may display in a display region 1130 a mode setting status indicating that an auto freeze mode has been set.

As another example, if a setting mode is determined as being a mode in which an auto freeze operation is not performed, the ultrasound apparatus 300 may display a mode setting status indicating that an auto freeze mode has not been set in the display region 1130.

Figure 12:
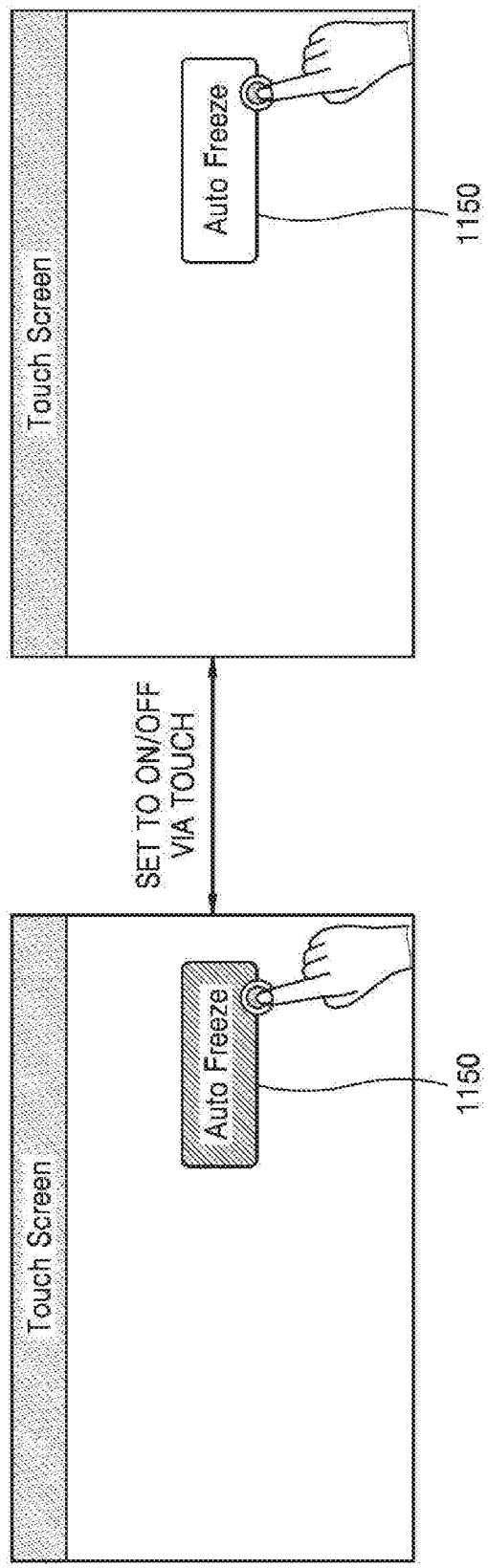
FIG. 12 is a diagram for explaining an example in which an ultrasound apparatus receives a user input, according to an embodiment.

FIG. 12 is a diagram for explaining an example in which the ultrasound apparatus 300 receives a user input, according to an embodiment.

The ultrasound apparatus 300 may display a screen as shown in FIG. 12.

According to an embodiment, the ultrasound apparatus 300 may display a screen for selecting whether a setting mode is determined as being a mode for performing an auto freeze operation.

For example, the ultrasound apparatus 300 may set a mode for performing an auto freeze operation to "on" or "off" according to the number of times a user input is performed on a predetermined region 1150. Furthermore, the ultrasound apparatus 300 may display, in the predetermined region 1150, whichever of the on and off modes to which the mode for performing an auto freeze operation is set.

Figure 13:
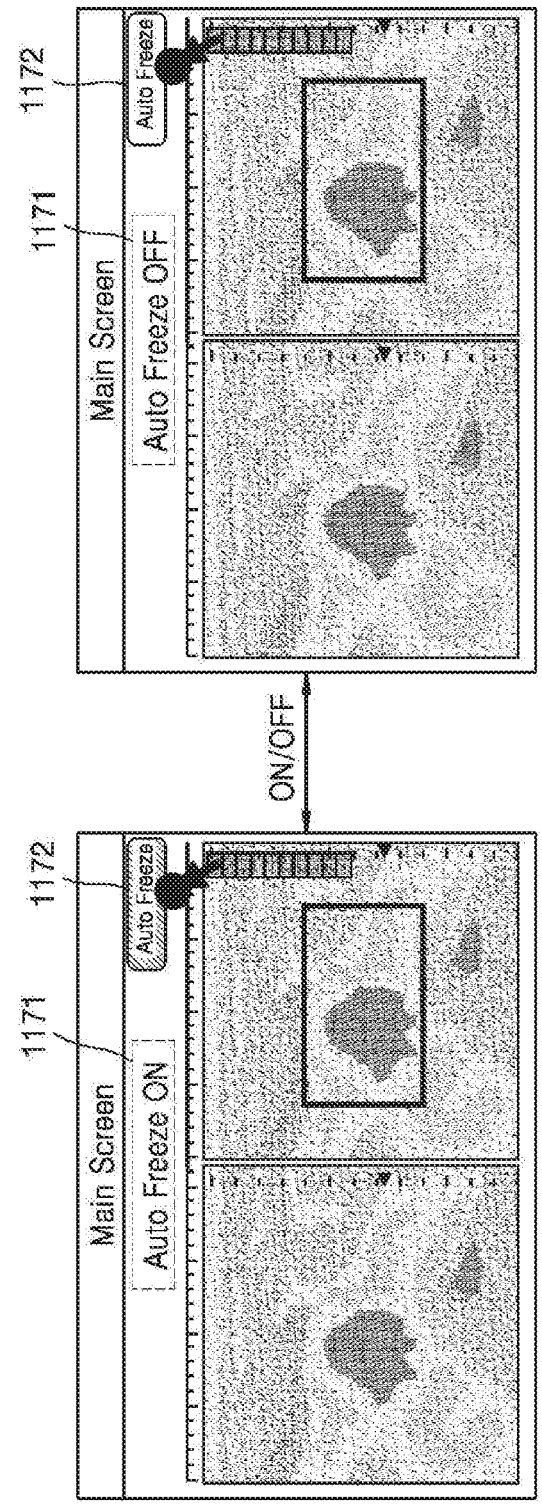
FIG. 13 is a diagram for explaining an example in which an ultrasound apparatus displays a current operating mode, according to an embodiment.

FIG. 13 is a diagram for explaining an example in which the ultrasound apparatus 300 displays a current operating mode, according to an embodiment.

When a setting mode is determined as being a mode for performing an auto freeze operation, the ultrasound apparatus 300 may display in a display region 1171 a mode setting status indicating that an auto freeze mode has been set. Furthermore, the ultrasound apparatus 300 may display a first menu 1172 used to receive a user touch input for determining whether an auto freeze mode is to be set. In addition, the ultrasound diagnosis apparatus 300 may indicate whether the auto freeze mode is set via the first menu 1172. For example, when an auto freeze mode is set, the first menu 1172 may be displayed using the color blue.

FIG. 14 is a diagram for explaining an example in which the ultrasound apparatus 300 performs a comparison between acquired images, according to an embodiment.

According to an embodiment, the ultrasound apparatus 300 may determine a variation by performing a comparison between first and second images 1411 and 1412 with a higher priority being placed on the overall change between the first and second images 1411 and 1412 than on individual changes between entities in the first and second images 1411 and 1412.

According to an embodiment, the ultrasound apparatus 300 may perform a comparison between images. For example, the ultrasound apparatus 300 may perform a comparison between the first and second images 1411 and 1412. The ultrasound apparatus 300 may determine a variation by performing a comparison between images with a higher priority being placed on the overall change between the images than on individual changes between entities in the images.

An example in which the ultrasound apparatus 300 performs a comparison between the first and second images 1411 and 1412 will now be described in more detail.

According to an embodiment, the ultrasound apparatus 300 may determine a degree of the overall change between the first and second images 1411 and 1412. For example, the ultrasound apparatus 300 may determine whether the overall shape 1440 of the second image 1412 moves as compared to the overall shape 1420 of the first image 1411 and the degree of movement, if the overall shape 1440 of the second image 1412 moves. If a region being measured moves as a whole due to shaking of hands of a measurer or other factors, the overall change between the first and second images 1411 and 1412 may occur to a large extent.

According to an embodiment, the ultrasound apparatus 300 may determine the degree of change between entities in the first and second images 1411 and 1412. For example, the ultrasound apparatus 300 may determine entities in the second image 1412 respectively corresponding to entities in the first image 1411 and then the degree of change between corresponding entities in the first and second images 1411 and 1412. When a change occurs between entities in the first and second images 1411 and 1412 due to a change inside an object (e.g., heartbeat), the change between the entities in the first and second images 1411 and 1412 may occur to a large extent. For example, the ultrasound apparatus 300 may determine a degree of change between a first entity 1410 and a second entity 1430 corresponding to the first entity 1410.

Furthermore, according to an embodiment, the ultrasound apparatus 300 may determine a variation by performing a comparison between the first and second images 1411 and 1412 with a higher priority being placed on the overall change between the first and second images 1411 and 1412 than on individual changes between entities in the first and second images 1411 and 1412.

According to another embodiment, the ultrasound apparatus 300 may determine a variation by performing a comparison between the first and second images 1411 and 1412 with a higher priority being placed on individual changes between entities in the first and second images 1411 and 1412 than on the overall change between the first and second images 1411 and 1412.

According to an embodiment, the ultrasound apparatus 300 may perform a comparison between images. For example, the ultrasound apparatus 300 may perform a comparison between the first and second images 1411 and 1412.

The ultrasound apparatus 300 may determine a variation by performing a comparison between images with a higher priority being placed on individual changes between entities in the images than on the overall change between the images.

An example in which the ultrasound apparatus 300 performs a comparison between the first and second images 1411 and 1412 will now be described in more detail.

According to an embodiment, the ultrasound apparatus 300 may determine a degree of the overall change between the first and second images 1411 and 1412. For example, the ultrasound apparatus 300 may determine whether the overall shape 1440 of the second image 1412 moves as compared to the overall shape 1420 of the first image 1411 and the degree of movement if the overall shape 1440 of the second image 1412 moves. If a region being measured moves as a whole due to shaking of hands of a measurer, etc., the overall change between the first and second images 1411 and 1412 may occur to a large extent.

According to an embodiment, the ultrasound apparatus 300 may determine a degree of change between entities in the first and second images 1411 and 1412. For example, the ultrasound apparatus 300 may determine entities in the second image 1412 respectively corresponding to entities in the first image 1411 and then a degree of change between corresponding entities in the first and second images 1411 and 1412. When a change occurs between entities in the first and second images 1411 and 1412 due to a change inside the object (e.g., heartbeat), the change between the entities in the first and second images 1411 and 1412 may occur to a large extent. For example, the ultrasound apparatus 300 may determine a degree of change between the first entity 1410 and the second entity 1430 corresponding to the first entity 1410.

Furthermore, according to an embodiment, the ultrasound apparatus 300 may determine a variation by performing a comparison between the first and second images 1411 and 1412 with a higher priority being placed on individual changes between entities in the first and second images 1411 and 1412 than on the overall change between the first and second images 1411 and 1412.

Embodiments may be implemented through non-transitory computer-readable recording media having recorded thereon computer-executable instructions such as program modules that are executed by a computer. The non-transitory computer-readable recording media may be any available media that can be accessed by a computer and include both volatile and nonvolatile media and both detachable and non-detachable media. Furthermore, the non-transitory computer-readable recording media may include computer storage media and communication media. The computer storage media include both volatile and nonvolatile and both detachable and non-detachable media implemented by any method or technique for storing information such as computer-readable instructions, data structures, program modules, or other data. The communication media typically embody computer-readable instructions, data structures, program modules, other data of a modulated data signal, or other transmission mechanism, and may include any information transmission media.

The above description is provided for illustration, and it will be understood by those of ordinary skill in the art that various changes in form and details may be made therein without departing from essential features and the spirit and scope of the present inventive concept as defined by the following claims. Accordingly, the above embodiments and all aspects thereof are examples only and are not limiting. For example, each component defined as an integrated component may be implemented in a distributed fashion. Likewise, components defined as separate components may be implemented in an integrated manner.

The scope of the present inventive concept is defined not by the detailed description thereof but by the appended claims, and all the changes or modifications within the scope of the appended claims and their equivalents will be construed as being included in the present inventive concept.

What is claimed is:

1. A method of acquiring an image by using ultrasound waves, the method comprising:
generating a plurality of consecutive images of an object from the ultrasound waves acquired by a probe;
determining variations representing differences between the plurality of consecutive images over time by performing a comparison between each of the plurality of consecutive images and its temporally adjacent image;
determining whether variations for a preset number of images from among the plurality of consecutive images are less than or equal to a preset value; and
automatically obtaining an elasticity image of the object by using the preset number of images having the variations that are less than or equal to the preset value.

2. The method of claim 1, further comprising displaying the elasticity image.

3. The method of claim 1, further comprising, before the generating of the plurality of consecutive images, receiving a user input for setting an operating mode with respect to whether the elasticity image is to be automatically obtained.

4. The method of claim 1, wherein the determining of the variations comprises determining the variations by using at least one of changes in shape of the object between the plurality of consecutive images and changes in distribution of elasticity values between the plurality of consecutive images.

5. The method of claim 1, wherein the generating of the plurality of consecutive images comprises generating the plurality of consecutive images of the object by using the ultrasound waves and storing the plurality of consecutive images in a temporary memory.

6. The method of claim 1, wherein the plurality of consecutive images comprise a brightness (B) mode image.

7. The method of claim 1, wherein the obtaining of the elasticity image of the object by using the preset number of images comprises obtaining the elasticity image by using an elastography technique.

8. The method of claim 1, wherein the determining of the variations comprises determining the variations by performing the comparison between the plurality of consecutive images with a higher priority being placed on an overall change between the plurality of consecutive images than on individual changes between entities in the plurality of consecutive images.

9. The method of claim 1, further comprising, after the obtaining of the elasticity image of the object by using the preset number of images, outputting, when the elasticity image is automatically obtained, a signal indicating that the elasticity image is obtained, by using at least one of vision, hearing, and a tactile sense.

10. A non-transitory computer-readable recording medium having recorded thereon a program for executing the method of claim 1 on a computer.

11. An ultrasound apparatus comprising:
an image processor configured to generate a plurality of consecutive images of an object from ultrasound waves acquired by a probe; and a controller configured to determine variations representing differences between the plurality of consecutive images over time by performing a comparison between each of the plurality of consecutive images and its temporally adjacent image, to determine whether variations for a preset number of images from among the plurality of consecutive images are less than or equal to a preset value, and to automatically obtain an elasticity image of the object by using the preset number of images having the variations that are less than or equal to the preset value.

12. The ultrasound apparatus of claim 11, further comprising a transceiver configured to transmit ultrasound signals to the object by the probe and receive echo signals generated in response to the ultrasound signals from the object by the probe,
wherein the image processor is further configured to generate the plurality of consecutive images by using the echo signals.

13. The ultrasound apparatus of claim 11, further comprising an input device configured to receive, before the generating of the plurality of consecutive images, a user input for setting an operating mode with respect to whether the elasticity image is to be automatically obtained.

14. The ultrasound apparatus of claim 11, wherein the controller is further configured to determine the variations by using at least one of changes in shape of the object between the plurality of consecutive images and changes in distributions of elasticity values between the plurality of consecutive images.

15. The ultrasound apparatus of claim 11, further comprising a memory configured to store the plurality of consecutive images of the object.

16. The ultrasound apparatus of claim 11, wherein the plurality of consecutive images comprise a brightness (B) mode image.

17. The ultrasound apparatus of claim 11, wherein the controller is further configured to determine the variations by performing the comparison between the plurality of consecutive images with a higher priority being placed on an overall change between the plurality of consecutive images than on individual changes between entities in the plurality of consecutive images.

18. The ultrasound apparatus of claim 11, further comprising a display configured to display an indication that the elasticity image is automatically obtained.

* * * * *